US006406878B1

(12) United States Patent
Hawkins et al.

(10) Patent No.: US 6,406,878 B1
(45) Date of Patent: Jun. 18, 2002

(54) METHODS FOR IDENTIFYING ENZYME INHIBITORS

(75) Inventors: Alastair Robert Hawkins, Newcastle upon Tyne; Heather Kim Lamb, Morpeth; Ian George Charles, Carshalton, all of (GB)

(73) Assignee: Arrow Therapeutics Limited, London (GB)

( * ) Notice: Subject to any disclaimer, the term of this patent is extended or adjusted under 35 U.S.C. 154(b) by 0 days.

(21) Appl. No.: 09/743,093

(22) PCT Filed: Jul. 5, 1999

(86) PCT No.: PCT/GB99/02134

§ 371 (c)(1),
(2), (4) Date: Feb. 2, 2001

(87) PCT Pub. No.: WO00/01844

PCT Pub. Date: Jan. 13, 2000

(30) Foreign Application Priority Data

Jul. 6, 1998 (GB) .............................................. 9814623

(51) Int. Cl.[7] ............................ C12Q 1/26; C12Q 1/32; C12Q 1/00
(52) U.S. Cl. ................................ 435/26; 435/25; 435/4
(58) Field of Search ................................ 435/26, 25, 4

(56) References Cited

U.S. PATENT DOCUMENTS 6,020,159 A  * 1/2000 Black et al.

FOREIGN PATENT DOCUMENTS

EP          0 832 978        4/1998

OTHER PUBLICATIONS

Hawkins et al, Molec. Gen. Genet., 214, 224–231, 1998.
Lamb et al, Molec. Gen. Genet, 227, 187–196, 1991.
Lamb et al, Biochem. J., 284, 181–187, 1992.
Wheeler et al, Biochem. J., 315, 195–205, 1996.
Beri et al, Nucl. Acids Res., 19, 7991–8001, 1987.
Hawkins et al, Gene, 110, 109–114, 1992.
Leech et al, J Biol. Chem, 270, 25827–25836, 1995.
Gunel–Ozcan et al, Microbiol. Pathogen, 23, 311–316, 1997.
Roberts et al, Nature, 393, 801–805, 1998.
Shujaath et al, Methods in Enzymol., 142, 306–314, 1987.
Moore et al, Biochem. J., 301, 297–304, 1994.
Moore et al, Biochem. J., 295, 277–285, 1993.
Gourley et al, J. Mol. Biol., 241, 488–491, 1994.
Pompliano et al. (1989). Probing lethal metabolic perturbations in plants with chemical inhibition of dehydroquinate synthase. J Am Chem Soc, 111 (5), pp 1866–1871.*
Myrvold et al. (1989). Chemical inhibition of dehydroquinate synthase. J Am Chem Soc, 111 (5), pp 1861–1866.*
Roberts, F. et al.: "Evidence for the shikimate pathway in apicomplexan parasites" Nature, vol. 393, (Jun. 1998) pp. 801–805.
Lamb, Heather K. et al.: "The QUTA activator and QUTR repressor proteins of *Aspergillus nidulans* interact to regulate transcription of the quinate utilization pathway genes" Microbiology (Reading, U. K.) (1996) 142(6), 1477–1490.

* cited by examiner

*Primary Examiner*—Ralph Gitomer
*Assistant Examiner*—Mahreen Chaudhry
(74) *Attorney, Agent, or Firm*—Nixon & Vanderhye P.C.

(57) ABSTRACT

A method for identifying an inhibitor of dehydroquinate synthase (DHQS) and/or dehydroquinase (DQ), which method comprises: i) contacting a test substance with DHQS and a substrate for DHQS and contacting the resulting reaction mixture with DQ, or contacting the test substance with DQ and a substrate for DQ; and ii) contacting the resulting reaction mixture with dehydroshikimate dehydratase (DHSD); and iii) determining whether the test substance inhibits the activity of DHQS or DQ.

15 Claims, 3 Drawing Sheets

METHODS FOR IDENTIFYING ENZYME INHIBITORS

FIELD OF THE INVENTION

This invention relates to methods for identifying substances capable of inhibiting the enzymes dehydroquinate synthase (DHQS) and/or dehydroquinase (DQ). It further relates to DHQS and/or DQ assays for identifying activity in a sample and to test kits for identifying substances capable of inhibiting dehydroquinate synthase and/or dehydroquinase.

BACKGROUND TO THE INVENTION

The shikimate pathway is an ancient pathway that is involved in primary and secondary metabolism and is found in all prokaryotes, many lower eukaryotes and plants, but not in mammalian cells. In primary metabolism the function of the pathway is to provide the precursors for the production of the aromatic amino acids and para-aminobenzoic acid. The shikimate pathway includes the enzymes and metabolites formed by converting 3-deoxy D-arabino-heptulosonic 3-phosphate (DAHP) to chorismic acid, the trifurication point for the three pathways leading to the production of tryptophane, tyrosine and phenylalanine.

In some microbial eukaryotes and prokaryotes, two of the products of the shikimate pathway (dehydroquinate and dehydroshikimate) are also shared by the quinate utilisation (qut) pathway (Hawkins et al., Molec. Gen. Genet. 214, 224–231, 1988). The qut pathway is a dispensable carbon utilisation pathway and the application of metabolic control analysis has shown that the common intermediates approximate an open pool and can be fluxed within and between the shikimate and qut pathways (Lamb et al., Molec. Gen. Genet. 227, 187–196, 1991; Lamb et al., Biochem. J. 284, 181–187, 1992 and Wheeler et al., Biochem. J. 315, 195–205, 1996). The biochemical relationships between the shikimate and quinate pathways are summarised in FIG. 1.

Overproduction of the gut pathway enzyme dehydroshikimate dehydratase in the absence of quinate causes an auxotrophic requirement for the aromatic amino acids due to flux of shikimate pathway dehyroshikimate to the gut pathway end point protocatechuic acid (Lamb et al., 1992). In *Aspergillus nidulans* for example it is advantageous to the growing mycelium that the qut pathway enzymes are only produced when quinate is available as a carbon source as their production in its absence would deplete flux in the essential shikimate pathway.

In *A.nidulans* the gut pathway is controlled by two transcription regulating proteins (designated QUTA and QUTR) that interact to ensure that the qut enzymes are only present when quinate is available (Beri et al., Nucleic Acids Res. 19, 7991–8001, 1987; Hawkins et al., Gene 110, 109–114, 1992; Hawkins et al., Gene 136, 49–54, 1993).

The importance of the shikimate pathway to cell viability is illustrated by experiments that result in the disruption of enzyme function. In plants, the shikimate pathway enzyme EPSP synthase has been targeted by a chemical inhibitor strategy that has resulted in the commercially successful broad range post-emergent herbicide called glyphosate.

In various microbial species, analysis of the shikimate pathway has been carried out genetically by the construction of mutants. When mutants of virulent prokaryotic or microbial eukaryotic species lacking enzymes at various steps in this pathway, the so-called aro⁻ mutants, are used to infect animals, their virulence is generally observed to be attenuated (Leech et al., J. Biol. Chem. 270, 25827–25836, 1995 and Gunel-Ozcan et al., *Microbial Pathogen.* 17, 169–174, 1997). After infection with aro⁻ mutants of *S.typhimurium*, mice are resistant to further challenge with the wild type strain. The probable reason for attenuation and immunological protection is that these aro⁻ mutants strains persist in the host-and replicate at a greatly reduced rate, thereby stimulating cell mediated immunity. The reason that aro⁻ mutants strains persist before being cleared is probably because they are able to derive sufficient quantities of the aromatic amino acids from the host cells to prevent immediate death. However, it is likely that their growth is limited by the availability of para-aminobenzoic acid.

Recently, the shikimate pathway has been characterised in apicomplexan parasites such as *Toxoplasma gondii, Plasmodium falciparum* (malaria) and *Cryptosporidium parvum* (Roberts et al., Nature 393, 801–805, 1998). Importantly, the growth of these parasites can be inhibited by the herbicide glyphosate, suggesting that the shikimate pathway will make a good target for the development of new anti-parasite agents.

The observations that both chemical and genetic inhibition of the shikimate pathway results in reduced cell viability has stimulated interest in the pathway as a possible target for drug therapy in acute microbial infection. It is likely that compounds which can inhibit the activity of shikimate enzymes will not cause cell death of the infecting microbe, but will result in attenuation in a manner analagous to the phenotype of shikimate pathway mutants. As antimicrobials, these compounds may be expected to induce stasis rather than cell lysis or death, allowing the infection to be cleared by the host's immune system. Such an outcome is desirable as it will ameliorate the absolute selective pressure to select for the growth of resistant mutants which would inevitably be the case if the compounds used caused cell death. Additionally this strategy may also result in a degree of immune protection which may prevent reinfection. As efficacious compounds are unlikely to kill any infecting microorganisms, then the risks of toxic shock caused by, for example, bacterial protein and cellular debris will be minimised when treatment is administered.

SUMMARY OF THE INVENTION

According to the present invention there is provided a method for identifying an inhibitor of dehydroquinate synthase (DHQS) and/or dehydroquinase (DQ) comprising:
(i) contacting a test substance with DHQS and a substrate for DHQS and contacting the resulting reaction mixture with DQ, or contacting the test substance with DQ and a substrate for DQ; and
(ii) contacting the resulting reaction mixture with dehydroshikimate dehydratase (DHSD); and
(iii) determining whether the test substance inhibits the activity of DHQS or DQ.

The invention also provides:
a method of identifying DHQS activity in a sample, comprising:

(i) contacting the sample with a substrate for DHQS and contacting the resulting reaction mixture with DQ;
(ii) contacting the resulting reaction mixture with DHSD; and
(iii) determining whether the sample exhibits DHQS activity;

a method of identifying DQ activity in a sample, comprising:
(i) contacting the sample with a substrate for DQ;
(ii) contacting the resulting reaction mixture with DHSD; and
(iii) determining whether the sample exhibits DQ activity;

a test kit suitable for use in identifying an inhibitor of DHQS, which kit comprises DHQS, a substrate for DHQS, DQ, DHSD and a buffer; and a test kit suitable for use in identifying an inhibitor of DQ, which kit comprises DQ, a substrate for DQ, DHSD and a buffer.

The invention thus provides flexible assays for dehydroquinate synthase (DHQS) and dehydroquinase (DQ). These assays couple the production of dehydroquinate (produced by dehydroquinate synthase) to either a type I or a type II dehydroquinase (which convert dehydroquinate to dehydroshikimate) and a dehydroshikimate dehydratase (which converts dehydroshikimate to protocatechuic acid). The product dehydroshikimate can be monitored at 237 nm, and/or the product protocatechuate can be monitored at either 290 nM or, after reaction with iron, at 547 nM. This means that the activity of the enzyme DHQS or DQ can be measured continuously at two different points in the uv spectrum or by a discontinuous assay in the visible spectrum.

The assay for DHQS and DQ can be used to identify inhibitors of DHQS and DQ. The fact that the assay for inhibitors can be carried out as a discontinuous assay in the visible spectrum has the advantage that cheap plastic microtitre plates can be used to detect the effects of specific compounds on DHQS and/or DQ activity. Also, the screen for inhibitor substances is not limited by the absorbance spectrum of the substance being tested because the activity of DHQS and DQ can be measured at different points in the uv and/or visible spectra. The assay is suitable for adaptation to 96 well and 384 well plate technologies and can be automated using liquid handling robots, allowing modern high throughput screening techniques to be applied. The invention therefore permits high through-put, flexible and inexpensive screening for substances which inhibit DHQS and DQ. This will increase the likelihood of potent bioavailable drugs being identified.

DETAILED DESCRIPTION OF THE INVENTION

Enzymes

Figure 1:
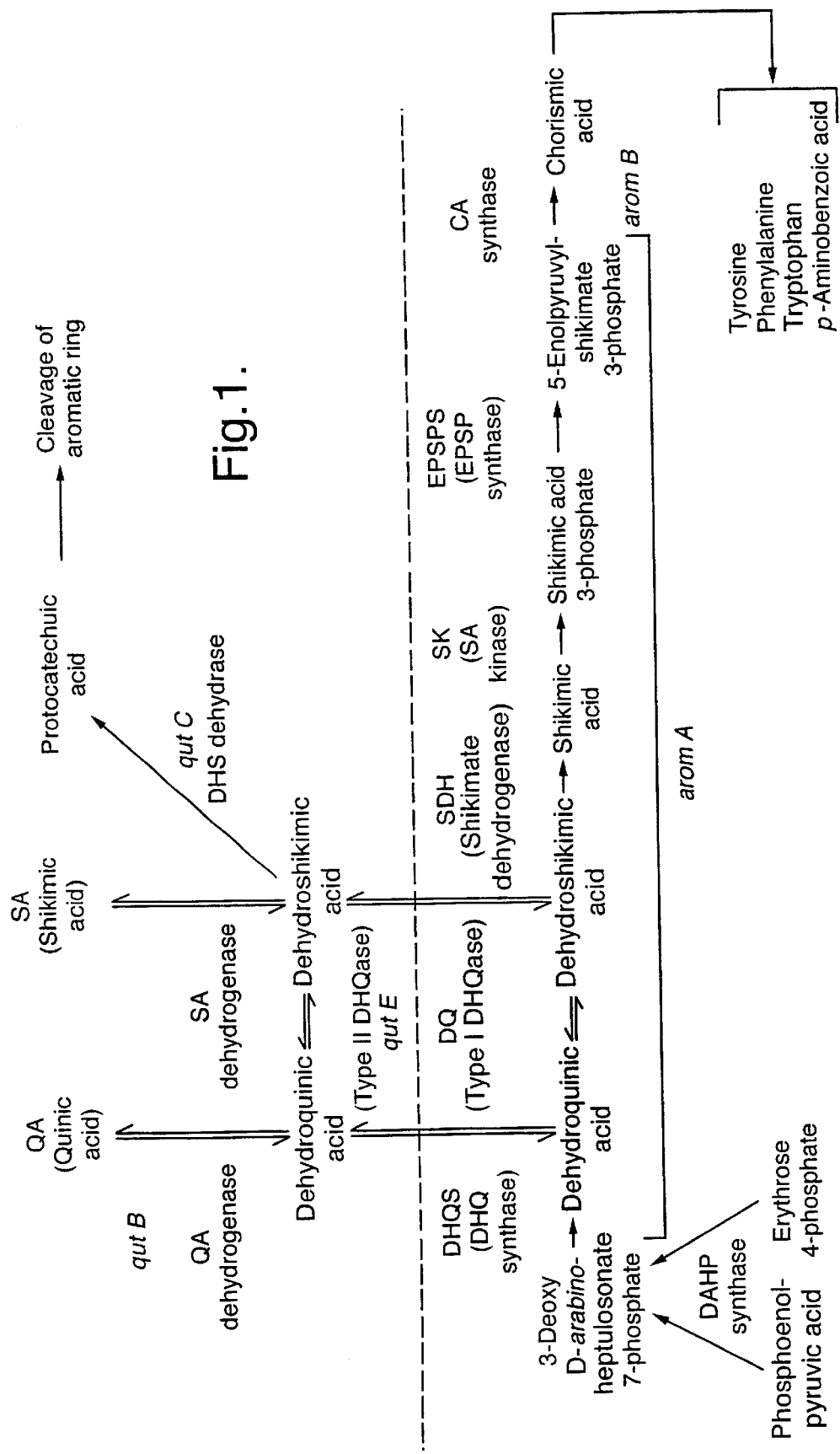
FIG. 1 shows the biochemical relationships between the shikimate and quinate pathways.

Any DHQS, DQ and DHSD may be used. The enzymes may be prokaryotic or eukaryotic. They may be obtained from prokaryotic or eukaryotic extracts, for example from a microbial extract. Alternatively, the enzymes may be produced recombinantly, from, for example, bacteria, yeast or higher eukaryotic cells such as insect cell lines.

(i) Dehydroquinate Synthase (DHQS)

The enzyme dehydroquinate synthase catalyses the second step in the shikimate pathway and is an ideal candidate as a target for chemotherapeutic design. The DHQS substrate is typically 3-deoxy D-arabino-heptulosonic 3-phosphate (DAHP). NAD is typically also present as a catalytic substrate for the enzymatic reaction.

A preferred enzyme is the DHQS from *A.nidulans*. The reason for this choice is that its reaction mechanism has been studied and characterised in great detail and recently the structure of this enzyme has been elucidated to a resolution of 1.8 angstroms. The N-terminal domain of the AROM protein from *A.nidulans* corresponding to the DHQS enzyme has been crystallised with an active site inhibitor and with one of the substrates $NAD^+$. Based on the crystal structure, key amino residues have been identified and their involvement in the reaction mechanism confirmed by site-directed mutagenesis. Large quantities of the wild-type enzyme can be purified with ease and mutant forms lacking enzyme activity can similarly be purified in bulk.

(ii) Dehydroquinase (DQ)

A type I or type II DQ may be used. Preferred examples of DQ are the DQ enzyme from *Salmonella typhi* and *Mycobacterium tuberculosis*. The crystal structures of the type I DQ from *Salmonella typhi* has been determined to 2.1 angstroms and the type II DQ from *Mycobacterium tuberculosis* to 2 angstroms. The details of the reaction mechanisms for each protein are known and the role of some of the amino acids implicated in the reaction mechanism have been investigated by site-directed mutagenesis.

Both of these enzymes can be purified in bulk and either enzyme can be used to catalyse the product of the dehydroquinate synthase enzyme, dehydroquinate to dehydroshikimate the substrate for dehydroshikimate dehydratase. The DQ substrate is thus dehydroquinic acid (dehydroquinate).

(iii) Dehydroshikimate Dehydratase (DHSD)

A preferred enzyme is the *A.nidulans* DHSD.

Assays

Any suitable format may be used for the assay for identifying an inhibitor of DHQS and/or DQ. The DHSD may be added to the mixture resulting from step (i). More usually, however, steps (i) and (ii) are conducted as a single step. Thus, the test substance may be contacted with DHQS, a substrate for DHQS, DQ and DHSD when testing for an inhibitor of DHQS. The test substance may be contacted with DQ, a substrate for DQ and DHSD when testing for a DQ inhibitor. The assay is generally therefore carried out in a single medium. Most preferably the assay is carried out in a single well of a plastic microtitre plate.

In practice, the enzyme reactions are commenced by addition of DHQS or a substrate for DHQS or, when testing for a DQ inhibitor, DQ or a substrate for DQ. An assay for a DHQS inhibitor may therefore be initiated by providing a medium, typically a buffered medium, containing a test substance and one of DHQS and a DHQS substrate, and adding the other of DHQS and the DHQS substrate to the medium. The medium may also contain DQ and DHSD. An assay for a DQ inhibitor may be initiated by providing a medium, such as a buffered medium, containing a test substance, one of DQ and a DQ substrate and, optionally, DHSD, and adding the other of DQ and the DQ substrate to the medium.

However, the assay for a DHQS inhibitor may be carried out by the sequential contact of DHQS, DQ and DHSD with the substance to be tested. In such an assay the substance to be tested would be contacted with either DHQS or a substrate for DHQS and the reaction initiated by the addition of a substrate for DHQS or DHQS respectively. DQ is then added to the reaction mixture or an aliquot could be removed from the reaction mixture and contacted with DQ in a separate mixture. Subsequently, DHSD can be added to the resulting reaction mixture or an aliquot could be removed from the reaction mixture and contacted with DHSD in a separate mixture. A sequential assay for a DQ inhibitor may be performed similarly.

The course of an assay can be followed by monitoring absorbance at 237 nm. Dehydroshikimate (dehydroshikimic acid) production can be monitored at this wavelength. The course of the assay may additionally or alternatively be followed by monitoring absorbance at 290 nm. The accumulation of the final product protocatechuic acid (PCA) can be monitored at this wavelength. Alternatively, the reaction can be terminated by adding a soluble ferric salt such as ferric chloride, for example $FeCl_3 \cdot 6H_2O$. The PCA reacts with the iron to form a complex which can be measured in the visible spectrum at 547 nm.

The assay can thus be followed by measuring the change in absorbance of the assay medium due to accumulation of the final product, protocatechuic acid (PCA).

The assay of the invention may be carried out at any temperature at which DHQS, DQ and DHSD, in the absence of any inhibitor are active. Typically, however, the assay will be carried out in the range of from 25° C. to 37° C.

The assay is typically carried out in a reaction buffer comprising NAD, a source of $Zn^{2+}$ ions and a source of $Mg^{2+}$ ions. The buffer may be a BisTrisPropane buffer. Preferably the buffer is 12.5 mM BisTrisPropane/acetate pH 7.0, 40 $\mu$M $ZnSO_4$ and 2.5 mM $MgSO_4$. The buffer can also contain 125 $\mu$M NAD for assay at 290 nm and 250 $\mu$M NAD for assay at 547 nm. An assay mixture could therefore be made up consisting of:

12.5 mM BisTrisPropane/acetate pH 7.0;
40 $\mu$M $ZnSO_4$;
2.5 mM $MgSO_4$;
125 $\mu$M NAD if the assay is to be monitored at 290 nm or 250 $\mu$M NAD if the assay is to be monitored at 547 nm;
40 $\mu$M DAHP if the assay is to be monitored at 290 nm or 286 $\mu$M DAHP if the assay is to be monitored at 547 nm;
1.0 units per ml of the *Salmonella typhi* type I DQ; and
1.0 units per ml of the *A.nidulans* DHSD.

An assay utilising such an assay mixture would typically be initiated by the addition of *A.nidulans* DHQS to a concentration of 0.1 units per ml.

As a control, the progress of the assay can be followed in the absence of the substance to be tested. Further control experiments can be carried out. For example, the ability of the substance being tested to inhibit the activity of DQ as well as DHQS can be identified by contacting the said substance with DQ and a substrate for DQ. The resulting reaction mixture can be contacted with DHSD, to determine the ability of the substance to inhibit the activity of DQ. Such a control will allow the skilled man to determine whether a substance inhibits DHQS or DQ or indeed both.

Additionally, a substance to be tested could be contacted with DHSD and a substrate for DHSD to determine the ability of the substance to inhibit the activity of DHSD.

Test Substances

A substance which inhibits the activity of DHQS and/or DQ may do so by binding to one or both of the enzymes. Such enzyme inhibition may be reversible or irreversible. An irreversible inhibitor dissociates very slowly from its target enzyme because it becomes very tightly bound to the enzyme, either covalently or non-covalently. Reversible inhibition, in contrast with irreversible inhibition, is characterised by a rapid dissociation of the enzyme-inhibitor complex.

The test substance may be a competitive inhibitor. In competitive inhibition, the enzyme can bind substrate (forming an enzyme-substrate complex) or inhibitor (enzyme-inhibitor complex) but not both. Many competitive inhibitors resemble the substrate and bind the active site of the enzyme. The substrate is therefore prevented from binding to the same active site. A competitive inhibitor diminishes the rate of catalysis by reducing the proportion of enzyme molecules bound to a substrate.

The inhibitor may also be a non-competitive inhibitor. In non-competitive inhibition, which is also reversible, the inhibitor and substrate can bind simultaneously to an enzyme molecule. This means that their binding sites do not overlap. A non-competitive inhibitor acts by decreasing the turnover number of an enzyme rather than by diminishing the proportion of enzyme molecules that are bound to substrate.

The inhibitor can also be a mixed inhibitor. Mixed inhibition occurs when an inhibitor both effects the binding of substrate and alters the turnover number of the enzyme.

A substance which inhibits the activity of DHQS or DQ may also do so by binding to the substrate. The substance may itself catalyze a reaction of the substrate, so that the substrate is not available to the enzyme. Alternatively the inhibitor may simply prevent the substrate binding to the enzyme.

Suitable candidate substances include antibody products (for example, monoclonal and polyclonal antibodies, single chain antibodies, chimaeric antibodies and CDR-grafted antibodies) which are specific for DHQS and/or DQ. Furthermore, combinatorial libraries, defined chemical identities, peptide and peptide mimetics, oligonucleotides and natural product libraries may be screened for activity as inhibitors of DHQS and/or DQ in assays such as those described below. The candidate substances may be used in an initial screen of, for example, ten substances per reaction, and the substance of these batches which show inhibition tested individually. Candidate substances which show activity in assays such as those described below can then be tested in in vivo systems, such as an animal model. Candidate inhibitors could be tested for their ability to attenuate microbial infection in mice.

Therapeutic Uses

Virulent prokaryotic or microbial eukaryotic species mutant for enzymes at various steps of the shikimate pathway are generally observed to be attenuated when used to infect animals. Furthermore, the apicomplexan parasites have been observed to be inhibited by the herbicide glyphosphate. The present invention can enable a substance to be identified which is capable of inhibiting the activity of one or both of two enzymes of the shikimate pathway, DHQS and DQ. In particular, such a substance may be used in a method of treating a microbial, especially bacterial, infection. Such substances may also be used for the manufacture of a medicament for use in the treatment of a microbial infection.

The formulation of a substance identified according to the invention will depend upon the nature of the substance identified. Typically a substance is formulated for clinical use with a pharmaceutically acceptable carrier or diluent. For example it may be formulated for typical parenteral, intravenous, intramuscular, subcutaneous, intraocular, transdermal or oral administration. A physician will be able to determine the required route of administration for a particular patient and the condition. The pharmaceutical carrier or diluent may be, for example, an isotonic solution.

The dose of substance used may be determined according to various parameters, especially according to the substance used; the age, weight and condition of the patient to be treated; the route of administration; and the required clinical regimen. A physician will be able to determine the required route of administration and dosage for any particular patient and condition.

Test Kits

The test kits of the invention comprise DQ and DHSD. When the test kit is intended for use in assaying for a DHQS inhibitor, the kit also contains DHQS and a substrate for DHQS. When the test kit is intended for use in assaying for a DQ inhibitor, the kit contains DQ and a DQ substrate.

The kits also contain a buffer. Typically the buffer comprises NAD, a source of $Zn^{2+}$ ions and a source of $Mg^{2+}$ ions. Preferably the buffer is 12.5mM BisTrisPropane/acetate pH 7.0, 40 $\mu$M $ZnSO_4$ and 2.5 mM $MgSO_4$. The buffer may also contain 125 $\mu$M NAD for assays which are to be monitored at 290 nm and 250 $\mu$M NAD for assays which are to be monitored at 547 nm. An soluble ferric salt may be provided, such as ferric chloride, which can be added to the PCA product formed as a result of the coupled enzyme reaction. The ferric chloride is typically in the form $FeCl_3.6H_2O$.

The following Example illustrates the invention.

EXAMPLE

Abbreviations

AN-DHQS *Aspergillus nidulans* dehydroquinate synthase.
STI *Salmonella typhi* type I dehydroquinase.
MTII *Mycobacterium tuberculosis* type II dehydroquinase.
ANII *Aspergillus nidulans* type II dehydroquinase.
AN-DHSD *Aspergillus nidulans* dehydroshikimate dehydratase.
DAHP 3-deoxy D-arabino-heptulosonic 3-phosphate.
NAD Nicotinamide Adenine Di-Nucleotide.

Materials

DAHP was purified according to the method of Shujaath et al., Methods in Enzymol. 142, 306–314, 1987. The AN-DHQS, STI, ANII, MTII and AN-DHSD were purified according to the protocols described in references Moore et al., Biochem. J. 301, 297–304, 1994; Moore et al., Biochem J. 295, 277–285, 1993; Gourley et al., J. Mol. Biol. 241, 488–491, 1994; and Wheeler et al., Biochem J. 315, 195–205, 1996. The buffer was 12.5 mM BisTrisPropane/acetate pH 7.0 containing 40 $\mu$M $ZnSO_4$ and 2.5 mM $MgSO_4$.

Methods

NAD, AN-DHQS, ANII/MTII and AN-DHSD enzymes were added to 200 $\mu$l aliquots of the buffer and thoroughly mixed by gentle pipetting. The substrate DAHP was pipetted directly into the wells of a microtitre plate immediately before initiating the reaction. The reactions were initiated by the addition of 50 $\mu$l of the enzyme/NAD mixture to the microtitre wells containing the substrate DAHP. The contents of the microtitre wells were mixed by being drawn up and expelled five times with a disposable plastic tip designed for use on a 200 $\mu$l adjustable pipette.

The microtitre plate was then transferred to a dry incubator set at 37° C. and incubated for 15 minutes. The microtitre plate was then removed from the incubator and 1 $\mu$l of a 1% (w/v) solution of $FeCl_3.6H_2O$ was added to each of the reaction mixtures. Addition of the iron to those mixtures containing all three enzymes caused an intense localised blue/black colour to appear. The individual reaction mixtures were mixed by drawing up and expelling each mixture five times with a disposable plastic tip designed for use on a 200 $\mu$l adjustable pipette. This resulted in the appearance of an even blue colour in solution which was then photographed.

Results

1. Control experiments were carried out to demonstrate that the blue colour formed by the complex of iron with protocatechuate is specifically formed due to the sequential action of the enzymes dehydroquinate synthase, dehydroquinase and dehydroshikimate dehydratase. The assays were carried out in triplicate using the full complement of three enzymes. These assays used the *S.typhi* type I dehydroquinase or the type II enzymes from *M. tuberculosis* or *A.nidulans* as alternate sources of the first linking enzyme. The assays were repeated in triplicate leaving out singly each of the three enzymes. The precise enzyme and substrate mixtures are shown in Table 1 below:

| | AN-DHQS | STI | MTII | ANII | AN-DHSD | Buffer (without NAD) | 2.5 mM NAD | 12 mM DAHP |
|---|---|---|---|---|---|---|---|---|
| 1 | 0.02 U | 0.2 U | 0 | 0 | 0.16 U | 200 $\mu$l | 2 $\mu$l | 2.5 $\mu$l |
| 2 | 0.02 U | 0 | 0.2 U | 0 | 0.16 U | 200 $\mu$l | 2 $\mu$l | 2.5 $\mu$l |
| 3 | 0.02 U | 0 | 0 | 0.2 U | 0.16 U | 200 $\mu$l | 2 $\mu$l | 2.5 $\mu$l |
| 4 | 0.02 U | 0 | 0 | 0 | 0.16 U | 200 $\mu$l | 2 $\mu$l | 2.5 $\mu$l |
| 5 | 0.02 U | 0 | 0 | 0.2 U | 0 | 200 $\mu$l | 2 $\mu$l | 2.5 $\mu$l |
| 6 | 0 | 0 | 0 | 0.2 U | 0.16 U | 200 $\mu$l | 2 $\mu$l | 2.5 $\mu$l |

Figure 2A:
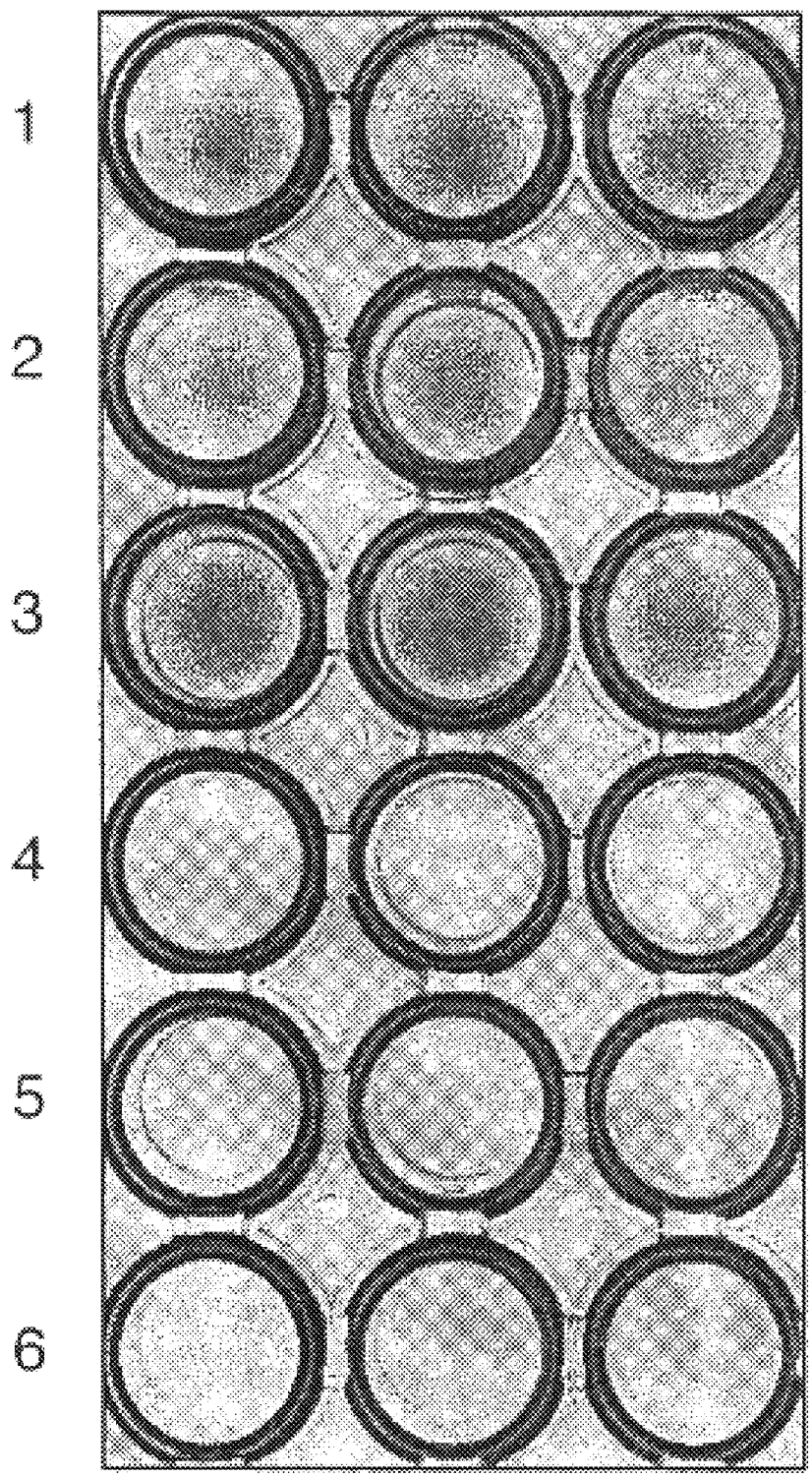
FIG. 2a shows the results obtained using the enzyme and substrate mixtures described in Table 1 below. The rows are numbered 1 to 6 according to mixtures 1 to 6 of Table 1.

FIG. 2a shows the result. If any one of the three enzymes is left out no blue colouration was produced, demonstrating that its formation was enzyme-dependent.

2. The full assay (using the *A.nidulans* enzyme) was repeated in triplicate with a two-fold serial dilution of the substrate DAHP in the range 286 $\mu$M to 9 $\mu$M. This is shown in Table 2 below:

| | AN-DHQS | ANII | AN-DHSD | Buffer | 2.5 mM NAD | 12 mM DAHP | Final DAHP concentration |
|---|---|---|---|---|---|---|---|
| 1 | 0.02 U | 0.2 U | 0.16 U | 200 μl | 2 μl | 5 μl | 286 (μM) |
| 2 | 0.02 U | 0.2 U | 0.16 U | 200 μl | 2 μl | 2.5 μl | 145 (μM) |
| 3 | 0.02 U | 0.2 U | 0.16 U | 200 μl | 2 μl | 2.5 μl of 1 in 2 dilution | 72 (μM) |
| 4 | 0.02 U | 0.2 U | 0.16 U | 200 μl | 2 μl | 2.5 μl of 1 in 4 dilution | 36 (μM) |
| 5 | 0.02 U | 0.2 U | 0.16 U | 200 μl | 2 μl | 2.5 μl of 1 in 8 dilution | 18 (μM) |
| 6 | 0.02 U | 0.2 U | 0.16 U | 200 μl | 2 μl | 2.5 μl of 1 in 16 dilution | 9 (μM) |

Figure 2B:
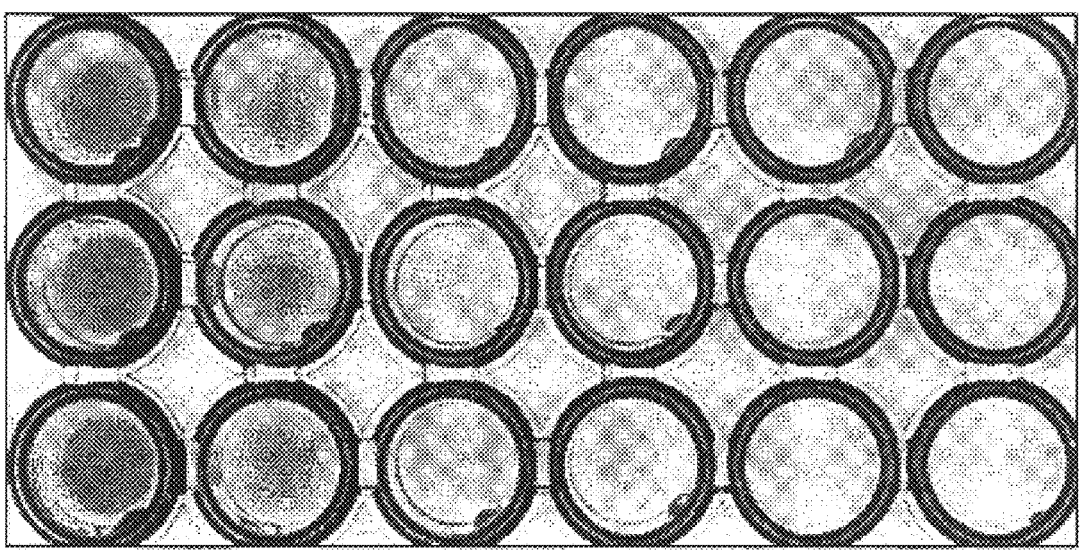
FIG. 2b shows the results obtained using the enzyme and substrate mixtures described in Table 2 below. The rows are numbered 1 to 6 according to mixtures 1 to 6 of Table 2.

The results are shown in FIG. 2b.

Discussion

These experiments show that the extent of blue colouration (product formation) is dependent on substrate concentration. Taken together the combined assays show that blue colouration is enzyme- and substrate-dependent. This means that the substrate concentration can be modulated to produce colour intensities that fall within the linear measuring range of the microtitre plate reader. Furthermore, the Example demonstrates that if any one of the enzymes is inhibited (either completely or partially) by a chemical addition to the assay then this would be easily detectable by an automated plate reader.

What is claimed is:

1. A method for identifying an inhibitor of dehydroquinate synthase (DHQS) and/or dehydroquinase (DQ), which method comprises:
    (i) contacting a test substance with DHQS and a substrate for DHQS and contacting the resulting reaction mixture with DQ, or contacting the test substance with DQ and a substrate for DQ; and
    (ii) contacting the resulting reaction mixture with dehydroshikimate dehydratase (DHSD); and
    (iii) determining whether the test substance inhibits the activity of DHQS or DQ by monitoring the amount of dehydroshikimate and/or protocatechuate by absorbance.

2. A method according to claim 1, wherein a buffered medium containing the test substance, DQ, DHSD and DHQS is provided and the enzyme reaction is then initiated by adding the DHQS substrate to the said buffered medium.

3. A method according to claim 1, wherein the DHQS is *Aspergillus nidulans* DHQS and/or the substrate for DHQS is 3-deoxy D-arabino-heptulosonic 3-phosphate (DAHP).

4. A method according to claim 1, wherein a buffered medium containing the test substance, DHSD and DQ is provided and the enzyme reaction is then initiated by adding the DQ substrate to the said buffered medium.

5. A method according to claim 1, wherein the DQ substrate is dehydroquinic acid.

6. A method according to claim 1, wherein the DQ is selected from the group consisting of type I dehydroquinase from *Salmonella typhi*, type II dehydroquinase from *Mycobacterium tuberculosis* and type II dehydroquinase from *Aspergillus nidulans*.

7. A method according to claim 1, wherein the DHSD is *Aspergillus nidulans* DHSD.

8. A method according to claim 1, wherein absorbance of dehydroshikimate is measured at 237 nm and/or absorbance of protocatechuate is measured at 290 nm.

9. A method according to claim 1, wherein the reaction mixture resulting from step (ii) is contacted with a soluble ferric salt.

10. A method according to claim 9, wherein absorbance of the reaction mixture in which the soluble ferric salt has been provided is measured at 547 nm.

11. A method of identifying DHQS activity in a sample, which method comprises:
    (i) contacting the sample with a substrate for DHQS and contacting the resulting reaction mixture with DQ;
    (ii) contacting the resulting reaction mixture with DHSD; and
    (iii) determining whether the sample exhibits DHQS activity by monitoring the amount of dehydroshikimate and/or protocatechuate by absorbance.

12. A method of identifying DQ activity in a sample, which method comprises:
    (i) contacting the sample with a substrate for DQ;
    (ii) contacting the resulting reaction mixture with DHSD; and
    (iii) determining whether the sample exhibits DQ activity by monitoring the amount of dehydroshikimate and/or protocatechuate by absorbance.

13. A test kit suitable for use in identifying an inhibitor of DHQS or DO, which kit comprises DQ, DHSD, a buffer and (a) DHQS and a substrate for DHQS or (b) a substrate for DQ.

14. A method according to claim 1, wherein a buffered medium containing the test substance, DQ, DHSD and the DHQS substrate is provided and the enzyme reaction is then initiated by adding DHQS to the said buffered medium.

15. A method according to claim 1, wherein a buffered medium containing the test substance, DHSD and the DQ substrate is provided and the enzyme reaction is then initiated by adding DQ to the said buffered medium.

* * * * *